US007469192B2

(12) United States Patent
Khuong et al.

(10) Patent No.: US 7,469,192 B2
(45) Date of Patent: Dec. 23, 2008

(54) PARALLEL PROFILE DETERMINATION FOR AN OPTICAL METROLOGY SYSTEM

(75) Inventors: Tri Thanh Khuong, San Jose, CA (US); Junwei Bao, Palo Alto, CA (US); Jeffrey A. Chard, Sunnyvale, CA (US); Wei Liu, Santa Clara, CA (US); Ying Zhu, Cupertino, CA (US); Sachin Deshpande, San Jose, CA (US); Pranav Sheth, San Jose, CA (US); Hong Qiu, Union City, CA (US)

(73) Assignee: Tokyo Electron Ltd., Tokyo (JP)

( * ) Notice: Subject to any disclaimer, the term of this patent is extended or adjusted under 35 U.S.C. 154(b) by 188 days.

(21) Appl. No.: 11/485,046

(22) Filed: Jul. 11, 2006

(65) Prior Publication Data

US 2008/0015812 A1    Jan. 17, 2008

(51) Int. Cl.
*G06F 19/00* (2006.01)
*G01B 11/00* (2006.01)

(52) U.S. Cl. .......................... 702/84; 702/189; 356/600

(58) Field of Classification Search .................. 702/84, 702/182, 189; 356/600, 601, 625
See application file for complete search history.

(56) References Cited

U.S. PATENT DOCUMENTS

| 6,609,086 | B1 * | 8/2003 | Bao et al. .................... 702/189 |
| 6,785,638 | B2 | 8/2004 | Niu et al. |
| 6,891,626 | B2 | 5/2005 | Niu et al. |
| 6,943,900 | B2 | 9/2005 | Niu et al. |
| 2004/0017574 | A1 | 1/2004 | Vuong et al. |
| 2004/0267397 | A1 | 12/2004 | Doddi et al. |
| 2005/0209816 | A1 | 9/2005 | Vuong et al. |
| 2007/0223011 | A1 * | 9/2007 | Jin et al. .................... 356/625 |

OTHER PUBLICATIONS

Li, L. (1996). "Formulation and comparison of two recursive matrix algorithms for modeling layered diffraction gratings," *Journal of the Optical Society of America A* 13:1024-1035.
Haykin, S. (1999). *Neural Networks*. 2nd edition, M. Horton ed., Prentice Hall: Upper Saddle River, New Jersey, 9 pages (Table of Contents).
Ausschnitt, C. P. (Feb. 23, 2004). "A New Approach to Pattern Metrology," *Proceedings of SPIE* 5375:51-65.
U.S. Appl. No. 11/485,048, filed Jul. 11, 2006 for Khong et al.

* cited by examiner

*Primary Examiner*—Bryan Bui
(74) *Attorney, Agent, or Firm*—Morrison & Foerster LLP

(57) ABSTRACT

A system to process requests for wafer structure profile determination from optical metrology measurements off a plurality of structures formed on one or more wafer includes a diffraction signal processor, a diffraction signal distributor, and a plurality of profile search servers. The diffraction signal processor is configured to obtain a plurality of measured diffraction signals of the plurality of structures. The diffraction signal distributor is coupled to the diffraction signal processor. The diffraction signal processor is configured to transmit the plurality of measured diffraction signals to the diffraction signal distributor. The plurality of profile search servers is coupled to the diffraction signal distributor. The diffraction signal distributor is configured to distribute the plurality of measured diffraction signals to the plurality of profile search servers. The profile search servers are configured to process in parallel the plurality of measured diffraction signals to determine profiles of the plurality of structures corresponding to the plurality of measured diffraction signals.

29 Claims, 11 Drawing Sheets

PARALLEL PROFILE DETERMINATION FOR AN OPTICAL METROLOGY SYSTEM

BACKGROUND

1. Field

The present application generally relates to optical metrology of a structure formed on a semiconductor wafer, and, more particularly, to parallel profile determination in optical metrology.

2. Related Art

In semiconductor manufacturing, periodic gratings are typically used for quality assurance. For example, one typical use of periodic gratings includes fabricating a periodic grating in proximity to the operating structure of a semiconductor chip. The periodic grating is then illuminated with an electromagnetic radiation. The electromagnetic radiation that deflects off of the periodic grating are collected as a diffraction signal. The diffraction signal is then analyzed to determine whether the periodic grating, and by extension whether the operating structure of the semiconductor chip, has been fabricated according to specifications.

In one conventional optical metrology system, the diffraction signal collected from illuminating the periodic grating (the measured-diffraction signal) is compared to a library of simulated-diffraction signals. Each simulated-diffraction signal in the library is associated with a hypothetical profile. When a match is made between the measured-diffraction signal and one of the simulated-diffraction signals in the library, the hypothetical profile associated with the simulated-diffraction signal is presumed to represent the actual profile of the periodic grating.

The library of simulated-diffraction signals can be generated using a rigorous method, such as rigorous coupled wave analysis (RCWA). More particularly, in the diffraction modeling technique, a simulated-diffraction signal is calculated based, in part, on solving Maxwell's equations. Calculating the simulated diffraction signal involves performing a large number of complex calculations, which can be time consuming and costly. Typically, a number of optical metrology measurements are performed for a number of sites in a wafer. The number of wafers that can be processed in a time period is proportional to the speed of determining the structure profile from the measured diffraction signals.

SUMMARY

In one exemplary embodiment, a system to process requests for wafer structure profile determination from optical metrology measurements off a plurality of structures formed on one or more wafer includes a diffraction signal processor, a diffraction signal distributor, and a plurality of profile search servers. The diffraction signal processor is configured to obtain a plurality of measured diffraction signals of the plurality of structures. The diffraction signal distributor is coupled to the diffraction signal processor. The diffraction signal processor is configured to transmit the plurality of measured diffraction signals to the diffraction signal distributor. The plurality of profile search servers is coupled to the diffraction signal distributor. The diffraction signal distributor is configured to distribute the plurality of measured diffraction signals to the plurality of profile search servers. The profile search servers are configured to process in parallel the plurality of measured diffraction signals to determine profiles of the plurality of structures corresponding to the plurality of measured diffraction signals.

DETAILED DESCRIPTION OF EXEMPLARY EMBODIMENT(S)

In order to facilitate the description of the present invention, a semiconductor wafer may be utilized to illustrate an application of the concept. The methods and processes equally apply to other work pieces that have repeating structures. Furthermore, in this application, the term structure when it is not qualified refers to a patterned structure.

1. Optical Metrology Tools

Figure 1A:
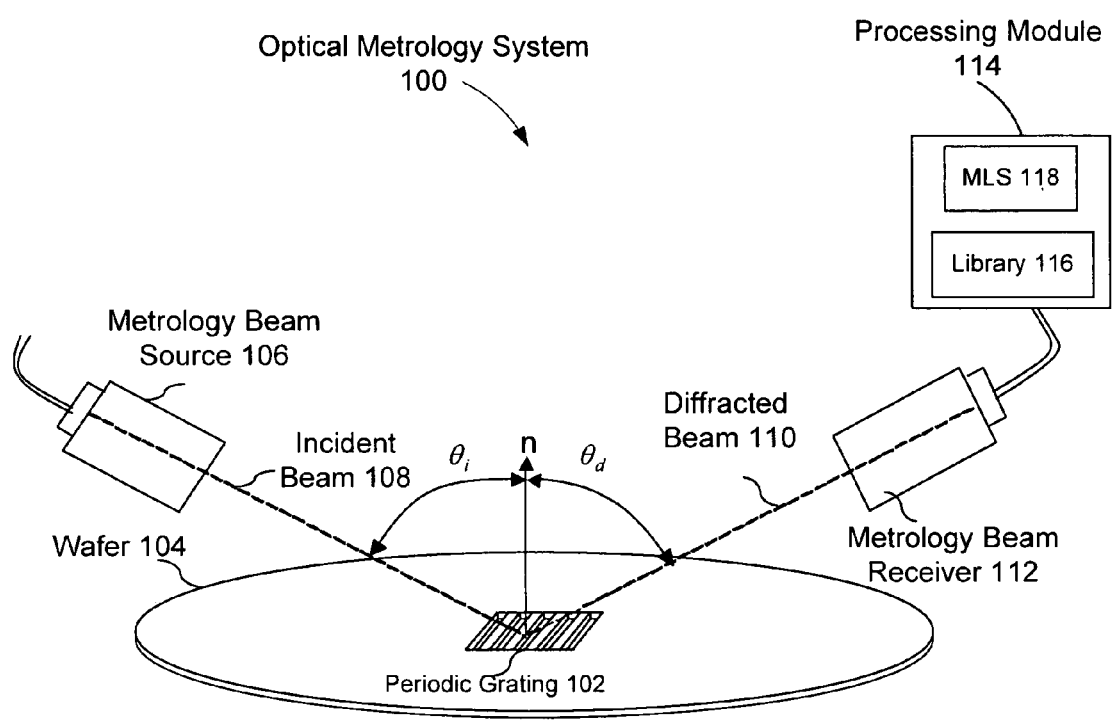
FIG. 1A is an architectural diagram illustrating an exemplary embodiment where optical metrology can be utilized to determine the profiles of structures on a semiconductor wafer.

With reference to FIG. 1A, an optical metrology system 100 can be used to examine and analyze a structure formed on a semiconductor wafer 104. For example, optical metrology system 100 can be used to determine one or more features of a periodic grating 102 formed on wafer 104. As described earlier, periodic grating 102 can be formed in a test pad on wafer 104, such as adjacent to a die formed on wafer 104. Periodic grating 102 can be formed in a scribe line and/or an area of the die that does not interfere with the operation of the die.

As depicted in FIG. 1A, optical metrology system 100 can include a photometric device with a source 106 and a detector 112. Periodic grating 102 is illuminated by an incident beam 108 from source 106. The incident beam 108 is directed onto periodic grating 102 at an angle of incidence $\theta_i$ with respect to normal $\vec{n}$ of periodic grating 102 and an azimuth angle $\Phi$ (i.e., the angle between the plane of incidence beam 108 and the direction of the periodicity of periodic grating 102). Diffracted beam 110 leaves at an angle of $\theta_d$ with respect to normal and is received by detector 112. Detector 112 converts the diffracted beam 110 into a measured diffraction signal, which can include reflectance, tan ($\Psi$), cos($\Delta$), Fourier coefficients, and the like. Although a zero-order diffraction signal is depicted in FIG. 1A, it should be recognized that non-zero orders can also be used. For example, see Ausschnitt, Christopher P., "A New Approach to Pattern Metrology," Proc. SPIE 5375-7, Feb. 23, 2004, pp 1-15, which is incorporated herein by reference in its entirety.

Optical metrology system 100 also includes a processing module 114 configured to receive the measured diffraction signal and analyze the measured diffraction signal. Processing module 114 is configured to determine one or more features of the periodic grating using any number of methods which provide a best matching diffraction signal to the measured diffraction signal. These methods are described below and include a library-based process or a regression based process using simulated diffraction signals obtained by rigorous coupled wave analysis and machine learning systems.

2. Library-based Process of Determining Feature of Structure

In a library-based process of determining one or more features of a structure, the measured diffraction signal is compared to a library of simulated diffraction signals. More specifically, each simulated diffraction signal in the library is associated with a hypothetical profile of the structure. When a match is made between the measured diffraction signal and one of the simulated diffraction signals in the library or when the difference of the measured diffraction signal and one of the simulated diffraction signals is within a preset or matching criterion, the hypothetical profile associated with the matching simulated diffraction signal is presumed to represent the actual profile of the structure. The matching simulated diffraction signal and/or hypothetical profile can then be utilized to determine whether the structure has been fabricated according to specifications.

Thus, with reference again to FIG. 1A, in one exemplary embodiment, after obtaining a measured diffraction signal, processing module 114 then compares the measured diffraction signal to simulated diffraction signals stored in a library 116. Each simulated diffraction signal in library 116 can be associated with a hypothetical profile. Thus, when a match is made between the measured diffraction signal and one of the simulated diffraction signals in library 116, the hypothetical profile associated with the matching simulated diffraction signal can be presumed to represent the actual profile of periodic grating 102.

The set of hypothetical profiles stored in library 116 can be generated by characterizing the profile of periodic grating 102 using a profile model. The profile model is characterized using a set of profile parameters. The set of profile parameters of the profile model are varied to generate hypothetical profiles of varying shapes and dimensions. The process of characterizing the actual profile of periodic grating 102 using the profile model and a set of profile parameters can be referred to as parameterizing.

Figure 2A:
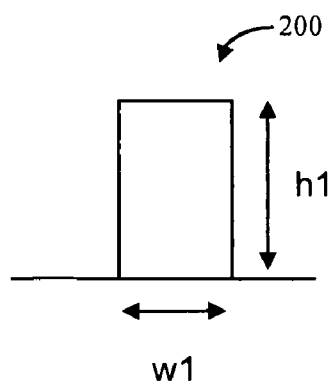
FIGS. 2A-2E depict various exemplary profile models.
Figure 2B:
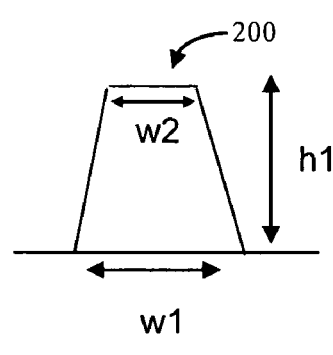
Figure 2C:
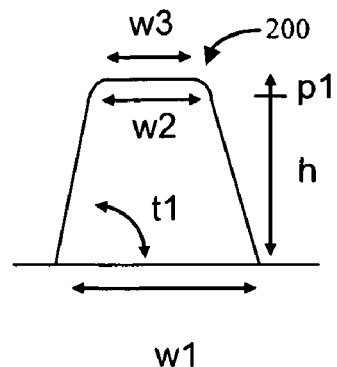
Figure 2D:
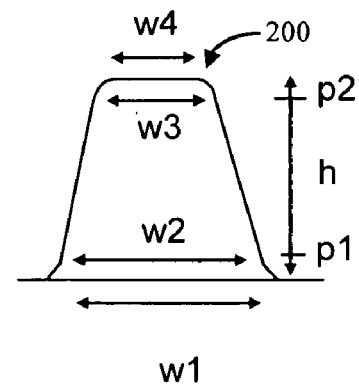
Figure 2E:
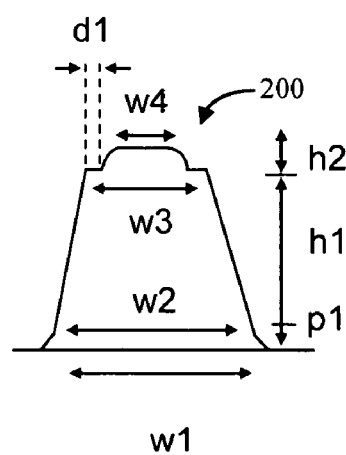

For example, as depicted in FIG. 2A, assume that profile model 200 can be characterized by profile parameters h1 and w1 that define its height and width, respectively. As depicted in FIGS. 2B to 2E, additional shapes and features of profile model 200 can be characterized by increasing the number of profile parameters. For example, as depicted in FIG. 2B, profile model 200 can be characterized by profile parameters h1, w1, and w2 that define its height, bottom width, and top width, respectively. Note that the width of profile model 200 can be referred to as the critical dimension (CD). For example, in FIG. 2B, profile parameter w1 and w2 can be described as defining the bottom CD (BCD) and top CD (TCD), respectively, of profile model 200.

As described above, the set of hypothetical profiles stored in library 116 (FIG. 1A) can be generated by varying the profile parameters that characterize the profile model. For example, with reference to FIG. 2B, by varying profile parameters h1, w1, and w2, hypothetical profiles of varying shapes and dimensions can be generated. Note that one, two, or all three profile parameters can be varied relative to one another.

With reference again to FIG. 1A, the number of hypothetical profiles and corresponding simulated diffraction signals in the set of hypothetical profiles and simulated diffraction signals stored in library 116 (i.e., the resolution and/or range of library 116) depends, in part, on the range over which the profile parameters and the increment at which the profile parameters are varied. The hypothetical profiles and the simulated diffraction signals stored in library 116 are generated prior to obtaining a measured diffraction signal from an actual structure. Thus, the range and increment (i.e., the range and resolution) used in generating library 116 can be selected based on familiarity with the fabrication process for a structure and what the range of variance is likely to be. The range and/or resolution of library 116 can also be selected based on empirical measures, such as measurements using AFM, X-SEM, and the like.

For a more detailed description of a library-based process, see U.S. patent application Ser. No. 09/907,488, titled GENERATION OF A LIBRARY OF PERIODIC GRATING DIFFRACTION SIGNALS, filed on Jul. 16, 2001, which is incorporated herein by reference in its entirety.

3. Regression-based Process of Determining Feature of Structure

In a regression-based process of determining one or more features of a structure, the measured diffraction signal is compared to a simulated diffraction signal (i.e., a trial diffraction signal). The simulated diffraction signal is generated prior to the comparison using a set of profile parameters (i.e., trial profile parameters) for a hypothetical profile. If the measured diffraction signal and the simulated diffraction signal do not match or when the difference of the measured diffraction signal and one of the simulated diffraction signals is not within a preset or matching criterion, another simulated diffraction signal is generated using another set of profile parameters for another hypothetical profile, then the measured diffraction signal and the newly generated simulated diffraction signal are compared. When the measured diffraction signal and the simulated diffraction signal match or when the difference of the measured diffraction signal and one of the simulated diffraction signals is within a preset or matching criterion, the hypothetical profile associated with the matching simulated diffraction signal is presumed to represent the actual profile of the structure. The matching simulated diffraction signal and/or hypothetical profile can then be utilized to determine whether the structure has been fabricated according to specifications.

Thus, with reference again to FIG. 1A, the processing module 114 can generate a simulated diffraction signal for a hypothetical profile, and then compare the measured diffraction signal to the simulated diffraction signal. As described above, if the measured diffraction signal and the simulated diffraction signal do not match or when the difference of the measured diffraction signal and one of the simulated diffraction signals is not within a preset or matching criterion, then processing module 114 can iteratively generate another simulated diffraction signal for another hypothetical profile. The subsequently generated simulated diffraction signal can be generated using an optimization algorithm, such as global optimization techniques, which includes simulated annealing, and local optimization techniques, which includes steepest descent algorithm.

The simulated diffraction signals and hypothetical profiles can be stored in a library 116 (i.e., a dynamic library). The simulated diffraction signals and hypothetical profiles stored in library 116 can then be subsequently used in matching the measured diffraction signal.

For a more detailed description of a regression-based process, see U.S. patent application Ser. No. 09/923,578, titled METHOD AND SYSTEM OF DYNAMIC LEARNING THROUGH A REGRESSION-BASED LIBRARY GENERATION PROCESS, filed on Aug. 6, 2001, which is incorporated herein by reference in its entirety.

4. Rigorous Coupled Wave Analysis

As described above, simulated diffraction signals are generated to be compared to measured diffraction signals. As will be described below, the simulated diffraction signals can be generated by applying Maxwell's equations and using a numerical analysis technique to solve Maxwell's equations. It should be noted, however, that various numerical analysis techniques, including variations of RCWA, can be used.

In general, RCWA involves dividing a hypothetical profile into a number of sections, slices, or slabs (hereafter simply referred to as sections). For each section of the hypothetical profile, a system of coupled differential equations is generated using a Fourier expansion of Maxwell's equations (i.e., the components of the electromagnetic field and permittivity ($\epsilon$)). The system of differential equations is then solved using a diagonalization procedure that involves eigenvalue and eigenvector decomposition (i.e., Eigen-decomposition) of the characteristic matrix of the related differential equation system. Finally, the solutions for each section of the hypothetical profile are coupled using a recursive-coupling schema, such as a scattering matrix approach. For a description of a scattering matrix approach, see Lifeng Li, "Formulation and comparison of two recursive matrix algorithms for modeling layered diffraction gratings," J. Opt. Soc. Am. A13, pp 1024-1035 (1996), which is incorporated herein by reference in its entirety. For a more detail description of RCWA, see U.S. patent application Ser. No. 09/770,997, titled CACHING OF INTRA-LAYER CALCULATIONS FOR RAPID RIGOROUS COUPLED-WAVE ANALYSES, filed on Jan. 25, 2001, which is incorporated herein by reference in its entirety.

5. Machine Learning Systems

The simulated diffraction signals can be generated using a machine learning system (MLS) employing a machine learning algorithm, such as back-propagation, radial basis function, support vector, kernel regression, and the like. For a more detailed description of machine learning systems and algorithms, see "Neural Networks" by Simon Haykin, Prentice Hall, 1999, which is incorporated herein by reference in its entirety. See also U.S. patent application Ser. No. 10/608,300, titled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety.

In one exemplary embodiment, the simulated diffraction signals in a library of diffraction signals, such as library 116 (FIG. 1A), used in a library-based process are generated using a MLS. For example, a set of hypothetical profiles can be provided as inputs to the MLS to produce a set of simulated diffraction signals as outputs from the MLS. The set of hypothetical profiles and set of simulated diffraction signals are stored in the library.

In another exemplary embodiment, the simulated diffractions used in regression-based process are generated using a MLS, such as MLS 118 (FIG. 1A). For example, an initial hypothetical profile can be provided as an input to the MLS to produce an initial simulated diffraction signal as an output from the MLS. If the initial simulated diffraction signal does not match the measured diffraction signal, another hypothetical profile can be provided as an additional input to the MLS to produce another simulated diffraction signal.

FIG. 1A depicts processing module 114 having both a library 116 and MLS 118. It should be recognized, however, that processing module 114 can have either library 116 or MLS 118 rather than both. For example, if processing module 114 only uses a library-based process, MLS 118 can be omitted. Alternatively, if processing module 114 only uses a regression-based process, library 116 can be omitted. Note, however, a regression-based process can include storing hypothetical profiles and simulated diffraction signals generated during the regression process in a library, such as library 116.

Figure 1B:
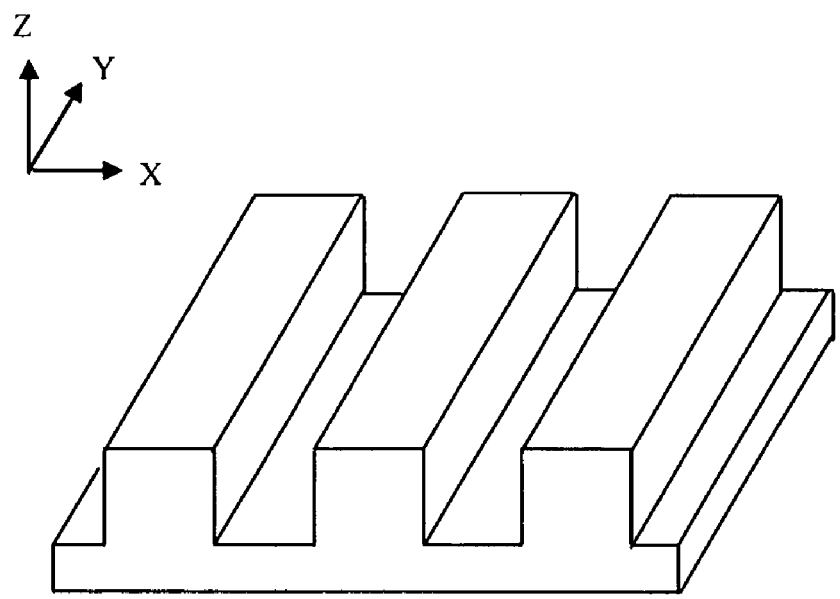
FIG. 1B depicts an exemplary one-dimension repeating structure.

The term "one-dimension structure" is used herein to refer to a structure having a profile that varies only in one dimension. For example, FIG. 1B depicts a periodic grating having a profile that varies only in one dimension (i.e., the x-direction). The profile of the periodic grating depicted in FIG. 1B varies in the z-direction as a function of the x-direction. However, the profile of the periodic grating depicted in FIG. 1B is assumed to be substantially uniform or continuous in the y-direction.

Figure 1C:
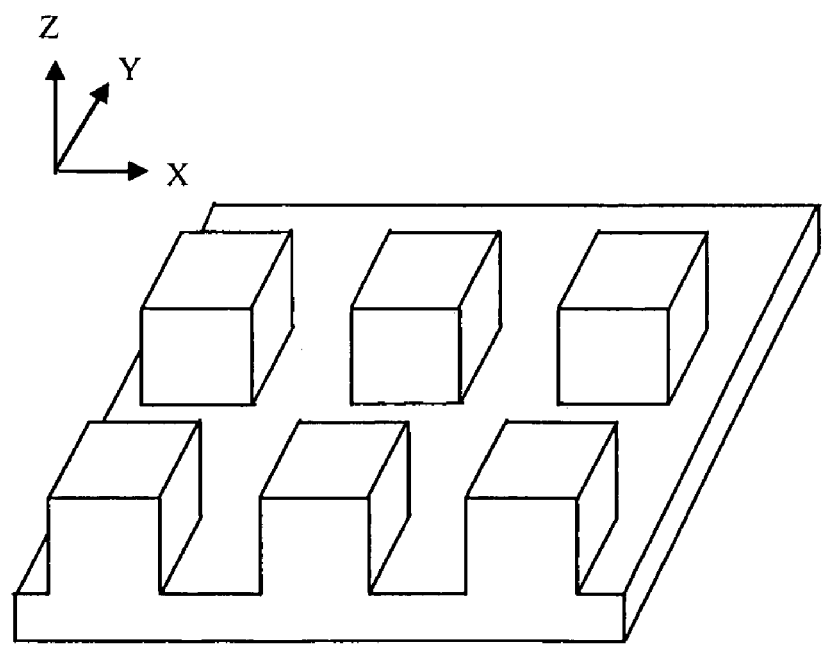
FIG. 1C depicts an exemplary two-dimension repeating structure.

The term "two-dimension structure" is used herein to refer to a structure having a profile that varies in two-dimensions. For example, FIG. 1C depicts a periodic grating having a profile that varies in two dimensions (i.e., the x-direction and the y-direction). The profile of the periodic grating depicted in FIG. 1C varies in the z-direction.

Figure 3A:
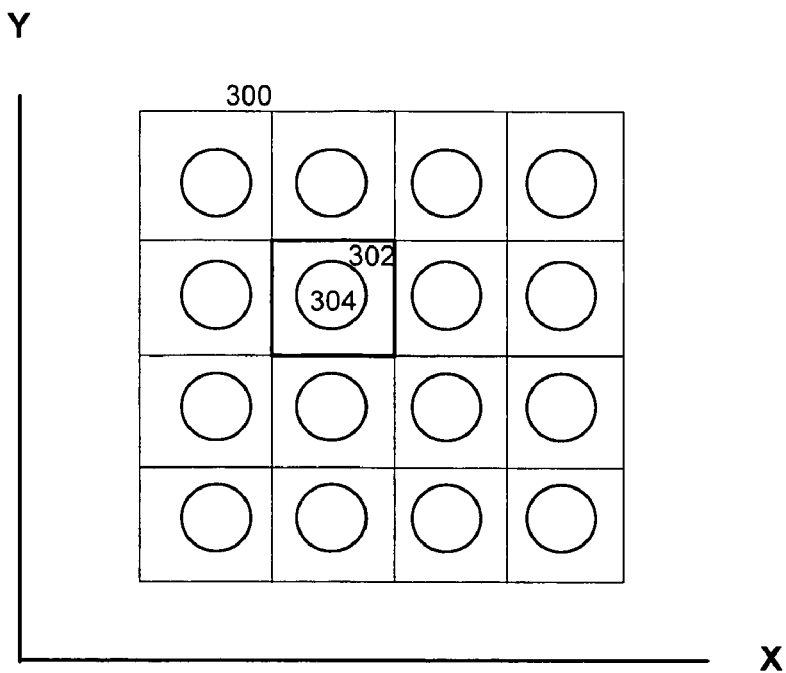
FIG. 3A depicts exemplary orthogonal grid of unit cells of a two-dimension repeating structure.

Discussion for FIGS. 3A, 3B, and 3C below describe the characterization of two-dimension repeating structures for optical metrology modeling. FIG. 3A depicts a top-view of exemplary orthogonal grid of unit cells of a two-dimension repeating structure. A hypothetical grid of lines is superimposed on the top-view of the repeating structure where the lines of the grid are drawn along the direction of periodicity. The hypothetical grid of lines forms areas referred to as unit cells. The unit cells may be arranged in an orthogonal or non-orthogonal configuration. Two-dimension repeating structures may comprise features such as repeating posts, contact holes, vias, islands, or combinations of two or more shapes within a unit cell. Furthermore, the features may have a variety of shapes and may be concave or convex features or a combination of concave and convex features. Referring to FIG. 3A, the repeating structure 300 comprises unit cells with holes arranged in an orthogonal manner. Unit cell 302 includes all the features and components inside the unit cell 302, primarily comprising a hole 304 substantially in the center of the unit cell 302.

Figure 3B:
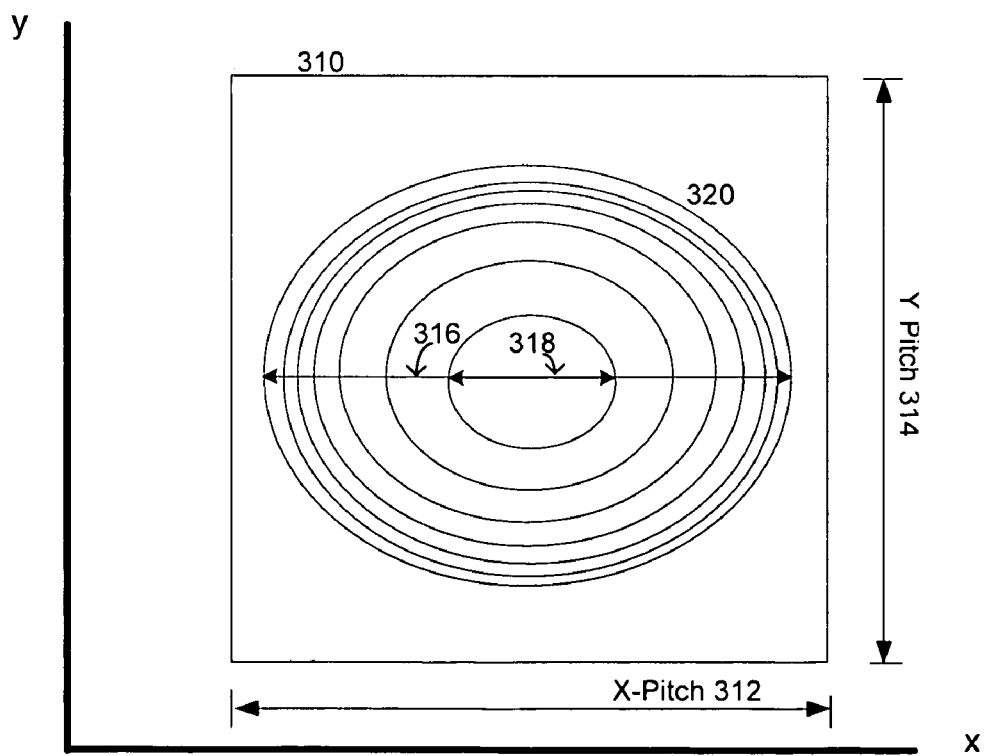
FIG. 3B depicts a top-view of a two-dimension repeating structure.

FIG. 3B depicts a top-view of a two-dimension repeating structure. Unit cell 310 includes a concave elliptical hole. FIG. 3B shows a unit cell 310 with a feature 320 that comprises an elliptical hole wherein the dimensions become progressively smaller until the bottom of the hole. Profile parameters used to characterize the structure includes the X-pitch 312 and the Y-pitch 314. In addition, the major axis of the ellipse 316 that represents the top of the feature 320 and the major axis of the ellipse 318 that represents the bottom of the feature 320 may be used to characterize the feature 320. Furthermore, any intermediate major axis between the top and bottom of the feature may also be used as well as any minor axis of the top, intermediate, or bottom ellipse, (not shown).

Figure 3C:
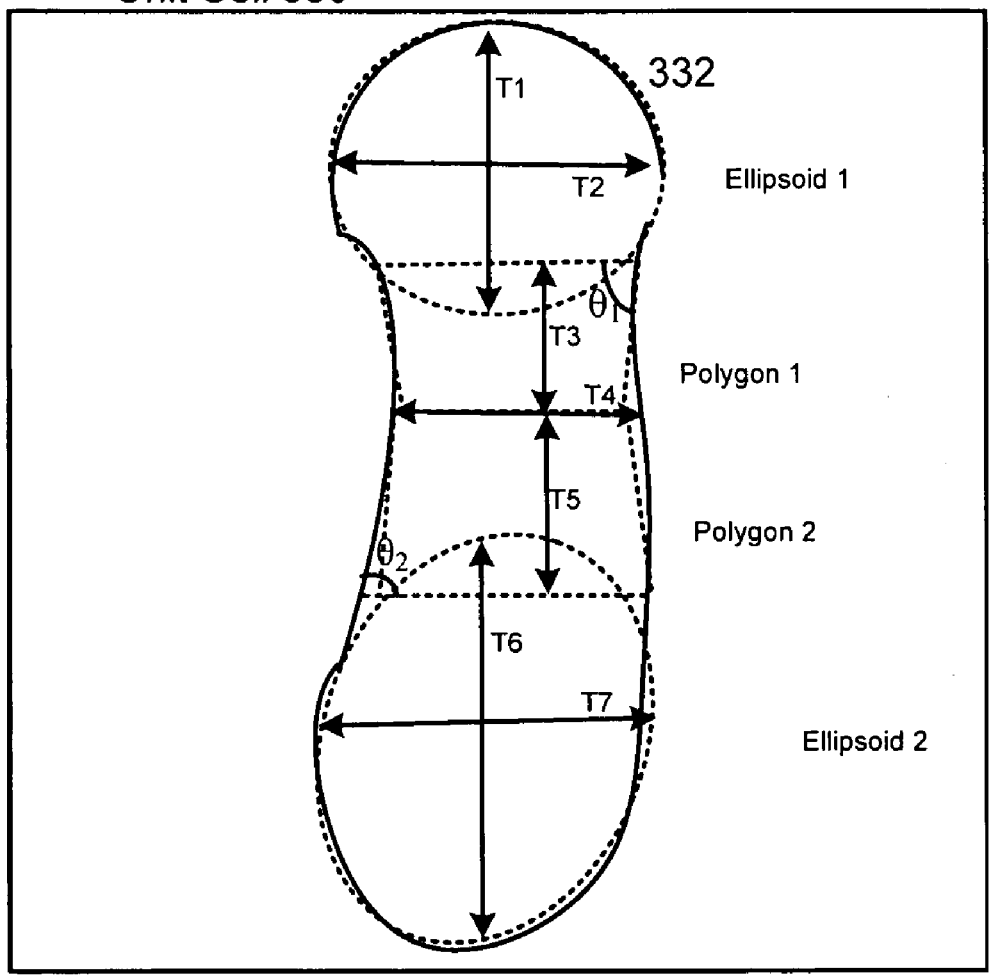
FIG. 3C is an exemplary technique for characterizing the top-view of a two-dimension repeating structure.

FIG. 3C is an exemplary technique for characterizing the top-view of a two-dimension repeating structure. A unit cell 330 of a repeating structure is a feature 332, an island with a peanut-shape viewed from the top. One modeling approach includes approximating the feature 332 with a variable number or combinations of ellipses and polygons. Assume further that after analyzing the variability of the top-view shape of the feature 322, it was determined that two ellipses, Ellipsoid 1 and Ellipsoid 2, and two polygons, Polygon 1 and Polygon 2 were found to fully characterize feature 332. In turn, parameters needed to characterize the two ellipses and two polygons comprise nine parameters as follows: T1 and T2 for Ellipsoid 1; T3, T4, and $\theta_1$ for Polygon 1; T4, T5, and $\theta_2$ for Polygon 2; T6 and T7 for Ellipsoid 2. Many other combinations of shapes could be used to characterize the top-view of the feature 332 in unit cell 330. For a detailed description of modeling two-dimension repeating structures, refer to U.S. patent application Ser. No. 11/061,303, OPTICAL METROLOGY OPTIMIZATION FOR REPETITIVE STRUCTURES, by Vuong, et al., filed on Apr. 27, 2004, which is incorporated in its entirety herein by reference.

6. Parallel Determination of Structure Profiles

Figure 4:
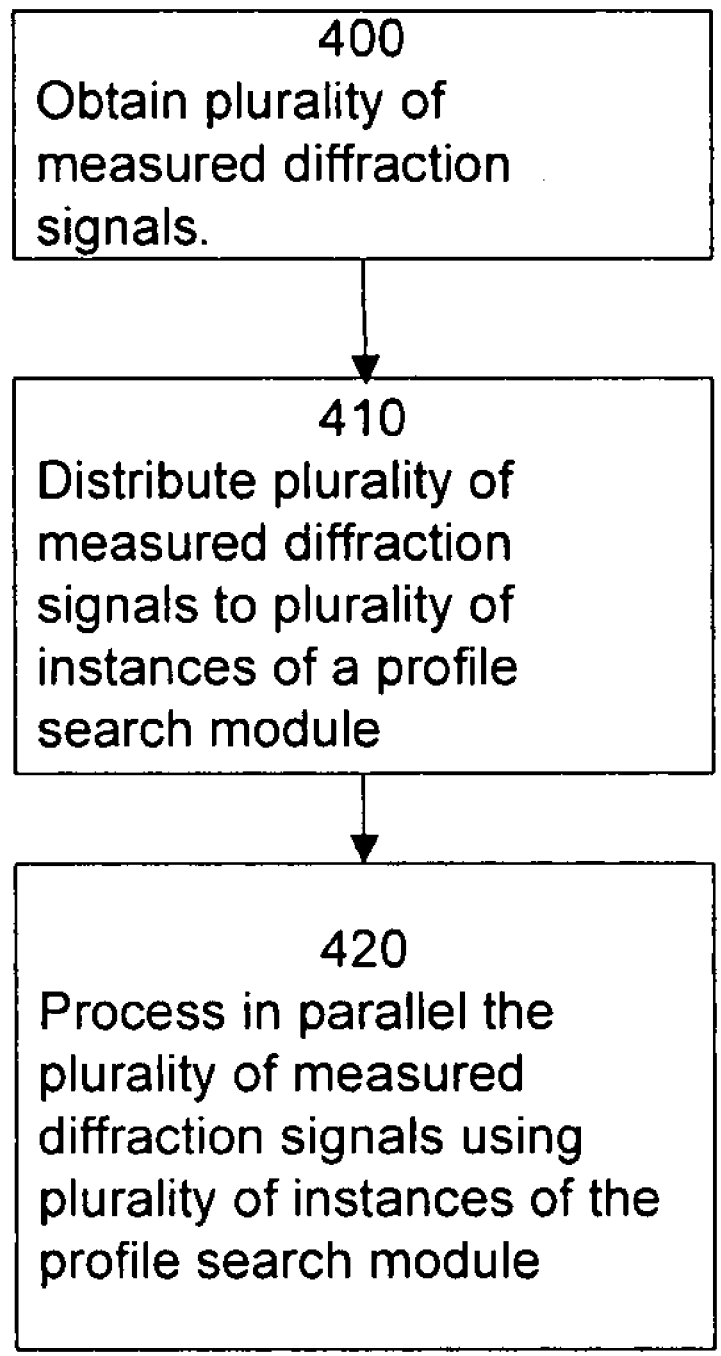
FIG. 4 is an exemplary flowchart for developing the capability of parallel processing for the determination of structure profiles from measured diffraction signals.

FIG. 4 is an exemplary flowchart for parallel processing for the determination of structure profiles from measured diffraction signals. In step 400, a plurality of measured diffraction signals of a plurality of structures formed on one or more wafers is obtained. In an integrated metrology environment, a number of measurements are typically performed on several sites on a wafer. Additionally, measurements can be obtained from multiple wafers of a lot or a run.

In step 410, the plurality of measured diffraction signals is distributed to a plurality of instances of a profile search module. The profile search module is designed with features and attributes that facilitate running the module in one or more processing threads of one or more computer systems and shall be referred to hereafter as parallel processing. Specifically, the profile search module is designed to perform the profile search and optimization at the following levels: on multiple computers, on multiple central processing units (CPU) within a computer, on multiple-cores within a multi-core CPU, or on multiple execution threads on a hyper-threaded CPU/core.

The typical design features for modules enabled for parallel processing comprises statelessness, machine independence, scalability, and fault tolerance. Statelessness means that the profile search module does not keep a history of requests to determine a profile from a given diffraction signal, such that the profile search module can process each request independently. Furthermore, if a request to a profile search module fails, then the request can be retried in another available profile search module in the same server or in another server. Machine independence enables the profile search module to run on most commercial computers. Scalability allows the profile search module to be deployed to meet throughput requirements. For example, many instances of the profile search module can be deployed on several threads of a multi-core CPU in a server and alternatively, many servers of a server farm can be deployed to meet throughput requirements. In addition, instances of the profile search module may use a distributed processing network including private and/or public networks. Fault tolerance means the ability to maintain reliable service even if program or server failures occur. For example, fault tolerance allows requests sent to unavailable servers to be redistributed to available servers.

In step 420, the plurality of measured diffraction signals is processing in parallel using the plurality of instances of the profile search module to determine profiles of the plurality of structures corresponding to the plurality of measured diffraction signals. A profile search module can be configured to determine a structure profile from a measured diffraction signal using a metrology data store or regression. The metrology data store can include a library or table comprising pairs of simulated diffraction signals and corresponding profiles or a machine learning system trained to determine a profile from a measured diffraction signal.

In one exemplary embodiment, one or more levels of schedulers are implemented to schedule the plurality of instances of the profile search module. A scheduler is a program that enables a computer system to schedule jobs or units of work, specifically in this application, to run the required number of instances of the profile search module or schedule the jobs in the available profile search modules. A job scheduler initiates and manages jobs automatically by processing prepared job control language statements or equivalents or through equivalent interaction with a human operator. The one or more layers of schedulers provide a single point of control for all the work in the one or more threads in one or more computers.

In one exemplary embodiment, a capability of monitoring the status of each instance of the profile search module is implemented. The status of each instance of the profile search module is used to make decisions for checking available profile search modules, restarting or shutting down an instance of a profile search module instance if conditions warrant such action.

In one exemplary embodiment, the capability to determine if processing for all measured diffraction signals for a wafer or lot or run have been completed is implemented. As noted above, in an integrated metrology environment, a number of measurements are typically performed on several sites in a wafer. In a typical serial processing setup, a measurement of the diffraction signal off the structure is made and the measured diffraction signal is sent to the profile search module where the structure profile is determined. With parallel processing, two or more measured diffraction signals are processed in parallel by the available instances of the profile search module.

Figure 5:
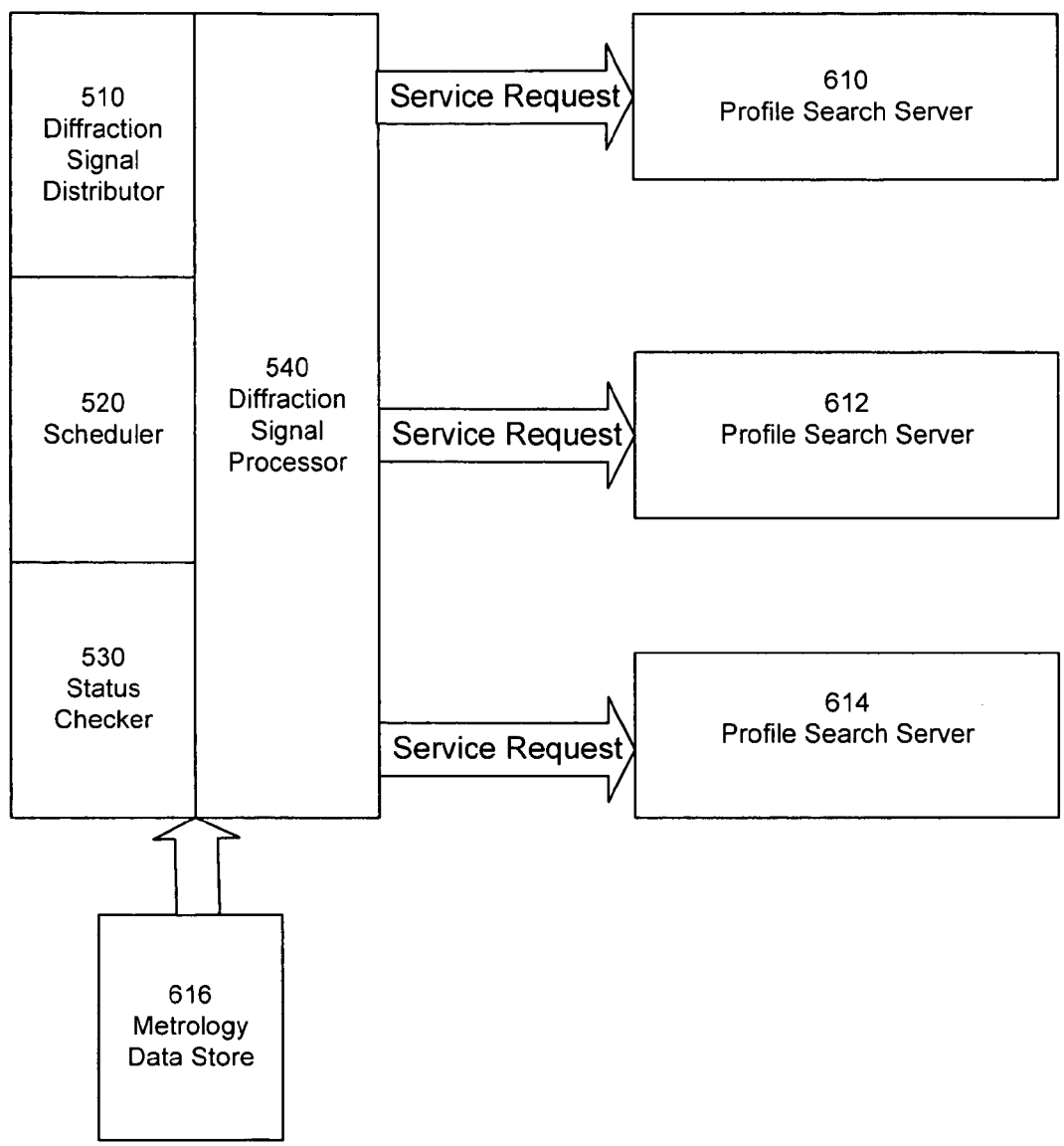
FIG. 5 is an exemplary architectural diagram of a system for performing parallel processing of multiple measured diffraction signals in one or more processing threads of one or more computer systems.

FIG. 5 is an exemplary architectural diagram of a system for performing parallel processing of multiple measured diffraction signals in one or more processing threads of one or more computer systems. The diffraction signal processor 540 controls the execution of the diffraction signal distributor 510, the scheduler 520, and the status checker 530. Additionally, in the present exemplary embodiment, the multiple profile search modules described above are implemented as profile search servers 610, 612, and 614. When a metrology data store is used, the diffraction signal processor 540 is further coupled to the metrology data store 616.

The diffraction signal processor 540 sends service requests to one or more of the profile search servers 610, 612, and 614. As mentioned above, the scheduler 520 determines the number of measured diffraction signals and allocates these diffraction signals to the available profile search modules (profile search servers 610, 612, 614). The status checker 530 communicates with all the instances of the profile search modules to determine availability and provides this information to the scheduler 520. The diffraction signal distributor 510 queries the number of measured diffraction signals waiting for processing and distributes these to the available instances of the profile search module.

Still referring to FIG. 5, as mentioned above, the metrology data store 616 can be a library or table comprising pairs of simulated diffraction signals and corresponding profiles or a machine learning system trained to determine a profile from a measured diffraction signal. Service requests are sent to one or more profile search servers 610, 612, and 614. When a metrology data store is used, a profile search server 610, 612, or 614 uses information from the metrology data store 616 to determine the best match simulated diffraction signal from the library, table, or trained machine learning system. In an alternative embodiment, more than one copy of the metrology data store 616 is available and may be coupled directly to a profile search server 610, 612, or 614, and also coupled to the diffraction signal processor 540. In still another embodiment, the library or machine learning system is loaded in memory every time a new profile search server is activated. As mentioned above, the profile search server may use regression to determine the structure profile.

Figure 6:
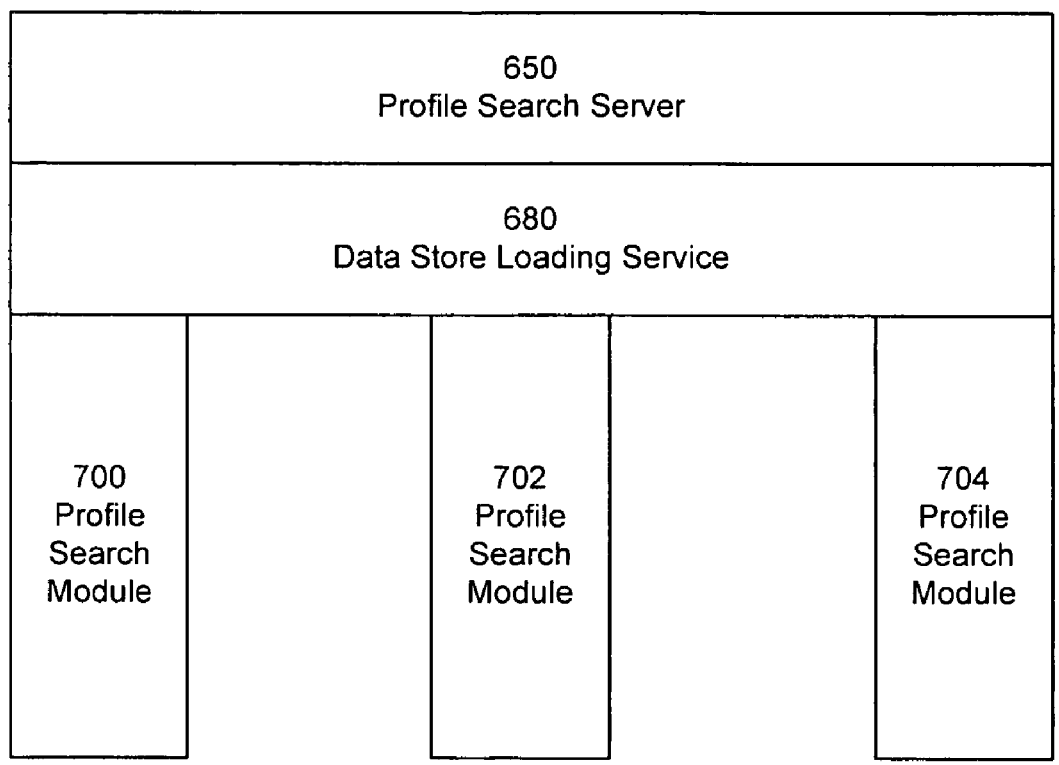
FIG. 6 is an exemplary architectural diagram of a profile search server for processing a measured diffraction signal.

FIG. 6 is an exemplary architectural diagram of a profile search server for processing measured diffraction signals. The profile search server 650 may be one of multiple computers that are part of a server farm or a central processing unit (CPU) within a computer, or a core within a multi-core CPU, or a group of execution threads on a hyper-threaded CPU/core. In one embodiment, a data store loading service 680 either provides a copy of the metrology data store such as a library or trained machine learning system or provides a link to the appropriate metrology data store. Coupled to the profile search server 650 are the profile search modules 700, 702, and 704. As mentioned above, the profile search module includes the logic to determine the best match structure profile from a measured diffraction signal or generate a structure profile from a measured diffraction signal using a trained machine learning system. In another embodiment, the profile search module includes the logic to determine the structure profile using regression.

Figure 7:
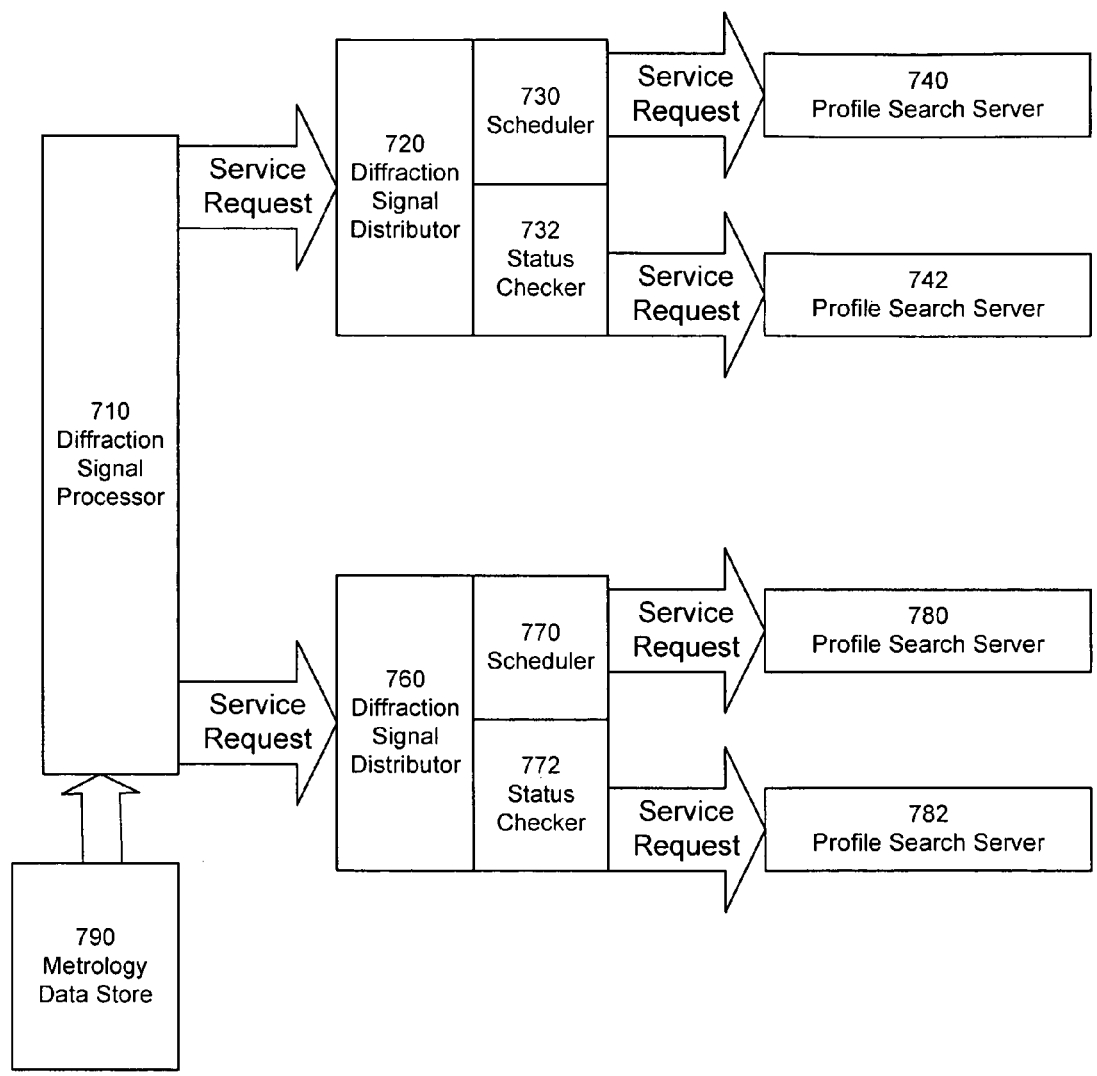
FIG. 7 is an exemplary architectural diagram of a system for profile search using multiple layers of parallel processing of multiple measured diffraction signals.

FIG. 7 is an exemplary architectural diagram of a system for profile search using multiple layers of parallel processing for measured diffraction signals. The system components have similar capabilities as the corresponding system components described in conjunction with FIG. 5. A diffraction signal processor 710 is coupled to one or more diffraction signal distributors 720 and 760, and to a metrology data store 790, if metrology data store is used. Coupled to the diffraction signal distributor 720 is a scheduler 730, a status checker 732, and one or more profile search servers 740 and 742. Similarly, coupled to the diffraction signal distributor 760 is a scheduler 770, a status checker 772, and one or more profile search servers 780 and 782. In an alternative embodiment, more that one copy of the metrology data store 790 is available and may be coupled directly to a profile search server 740, 742, 780, or 782. Similarly, in another embodiment, the library or machine learning system may be loaded in memory every time a new profile search server is activated.

Figure 8:
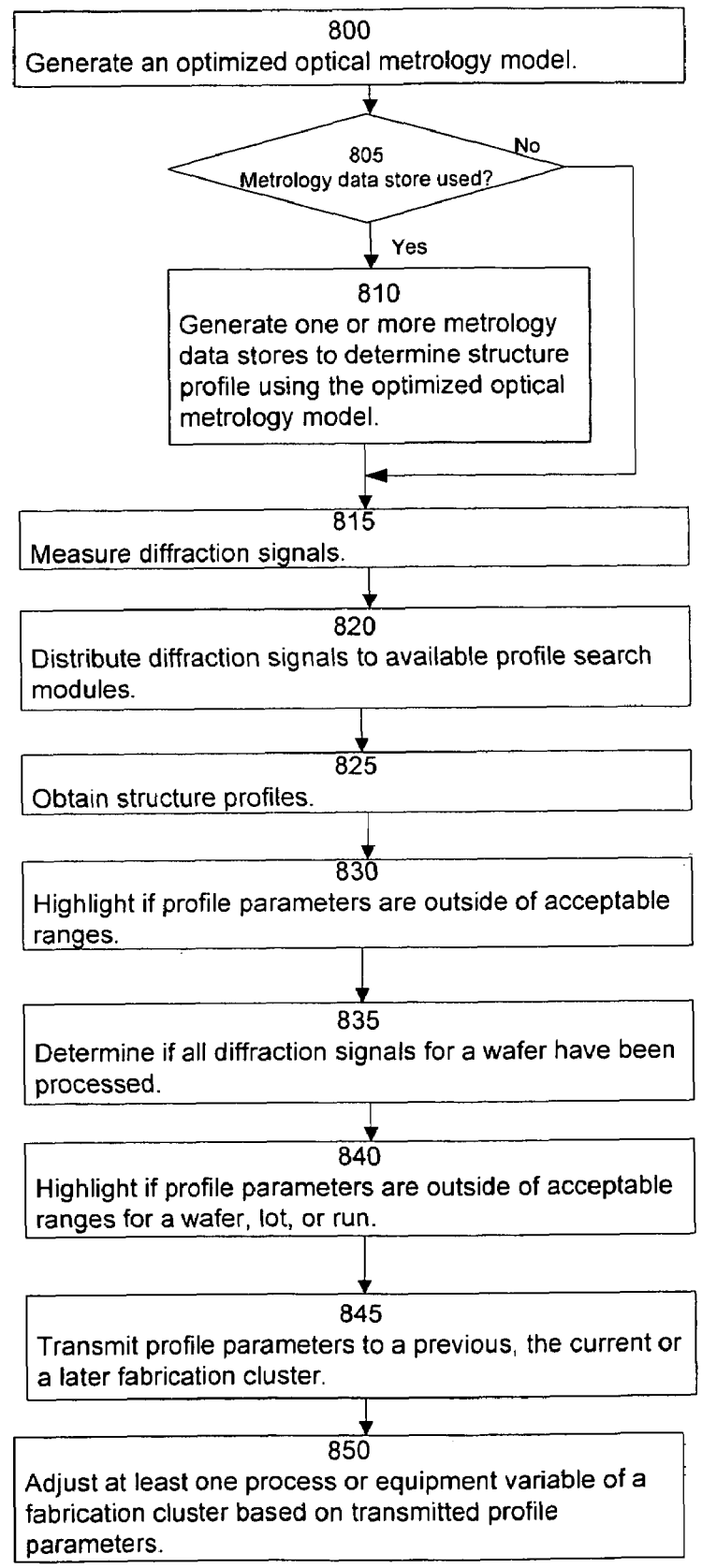
FIG. 8 is an exemplary flowchart for parallel processing of multiple measured diffraction signals by using a real time profile estimator or by using metrology data stores and using the obtained profile parameters in automated process and equipment control.

FIG. 8 is an exemplary flowchart for parallel processing of multiple measured diffraction signals with a real time profile estimator or by using metrology data stores and using the obtained profile parameters in automated process and equipment control. In step 800, an optimized optical metrology model is generated. For a detailed description of optimizing an optical metrology model, refer to U.S. patent application Ser. No. 10/206,491, OPTIMIZED MODEL AND PARAMETER SELECTION FOR OPTICAL METROLOGY, by Vuong, et al., filed on Jun. 27, 2002, which is incorporated in its entirety herein by reference.

If a metrology data store is used, step 805, one or more metrology data stores to determine structure profiles using the optimized optical metrology model are generated in step 810. For generation of a library, see U.S. Pat. No. 6,913,900, entitled GENERATION OF A LIBRARY OF PERIODIC GRATING DIFFRACTION SIGNAL, by Niu, et al., issued on Sep. 13, 2005, which is incorporated in its entirety herein by reference. For generation of a trained machine learning system, see also U.S. patent application Ser. No. 10/608,300, titled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety. As mentioned above, when regression is used in determining the profile from the measured diffraction signal, then one or more metrology data stores are not needed.

Referring to FIG. 8, in step 815, diffraction signals are measured off the wafer structure. This measurement may be done with a reflectometer, an ellipsometer, and the like. In step 820, the measured diffraction signals are distributed to available profile search modules. Available profile search modules are instances of the profile search module that are active and not busy determining the profile for a diffraction signal. An instance of the profile search module may be inactive due to an operating system, hardware, or program problems. In another embodiment, available profile search modules may be instances of the profile search module that are active, not busy determining the profile for a diffraction signal, and has a library or table already loaded in memory or local storage. The preloaded library or table may be a critical requirement for a profile search module to be considered available, especially when the library is large. In step 825, the structure profiles are determined by using the metrology data store or by regression.

When the metrology data store is used, the profiles are determined by getting the best match simulated diffraction signal in a library or table to the measured diffraction signal or by using a trained machine learning system that outputs a profile based on an input measured diffraction signal. When regression is used to determine the profile for a measured diffraction signal, the logic programmed in the profile search module includes the method described above under regression.

In step 830, selected profile parameters are compared to acceptable ranges established for the application and highlighted or flagged if these are outside of the acceptable ranges. For example, assume the selected parameter is a bottom critical dimension (BCD), and has a determined value of 50 nanometers (nm). If the acceptable range for the BCD is 35 to 45 nm, then the structure would be highlighted or flagged as being outside of the acceptable range.

Still referring to FIG. 8, in step 835, completion of profile determination of all measured diffraction signals for all the sites measured in the wafer is determined. A wafer is typically measured in a plurality of sites based on the requirements of the application. Thus, completion of profile determination is critical for quality control analysis and data gathering of wafer, lot, run, and recipe statistics.

In step 840, a wafer, a lot, a run, or a specified group of wafers may be highlighted or flagged if the determined values of selected profile parameters are outside of the acceptable ranges. In step 845, the determined profile parameters and identification (ID) data such as wafer ID, lot ID, run ID or other grouping IDs are transmitted to a previous fabrication cluster, the current fabrication cluster, or a later fabrication cluster. For example, if the current fabrication cluster is an etch fabrication cluster, the previous fabrication cluster may be a photolithography fabrication cluster, and a later fabrication cluster may be deposition fabrication cluster.

In step 850, at least one profile parameter in the transmitted information comprising profile parameters is used to adjust one process or equipment variable in the receiving fabrication cluster. Using the example above regarding the BCD after an etch process step, assume the acceptable range is 35 to 45 nm and the determined value of the BCD is 45 nm. The determined profile parameters including the BCD may be transmitted to the previous photolithography fabrication cluster such that the BCD may be used to adjust the focus and/or dose in the exposure process step. The profile parameters including the BCD may be sent to the current etch step and used to adjust the etchant concentration, time of etching, or some other variable in the etch equipment. The same profile parameters including the BCD may be sent to the later deposition process step where the deposition temperature or pressure in the chamber may be adjusted.

Figure 9:
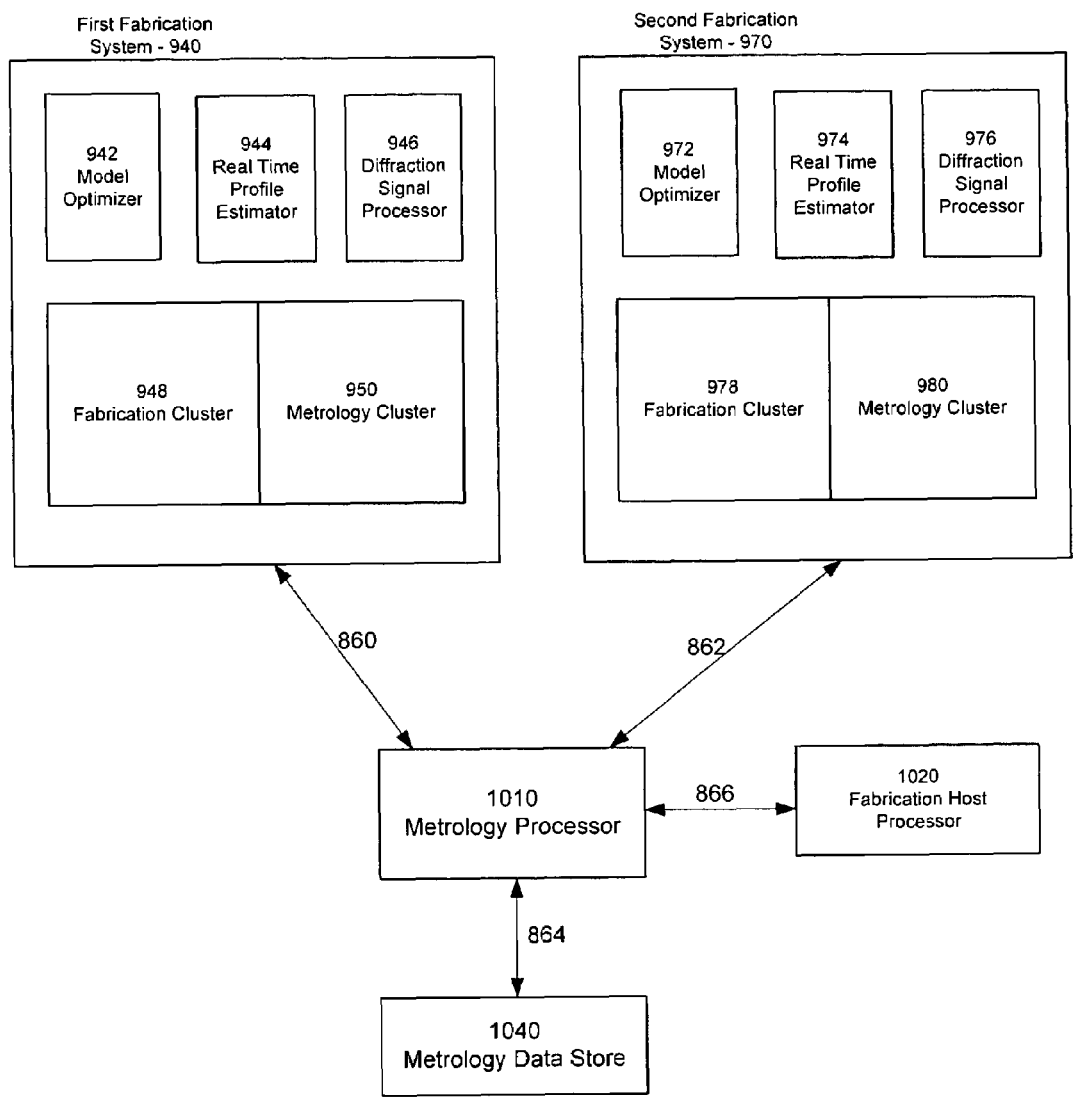
FIG. 9 is an exemplary architectural diagram for linking two or more fabrication systems with a metrology processor to determine profile parameters of wafer structures.

FIG. 9 is an exemplary architectural diagram for linking two or more fabrication systems with a metrology processor to determine profile parameters of wafer structures. A first fabrication system 940 includes a model optimizer 942, a real time profile estimator 944, diffraction signal processor 946, a fabrication cluster 948, and a metrology cluster 950. The metrology cluster 950 may include a reflectometer, an ellipsometer, or critical dimension scanning electron microscope (CDSEM).

The real time profile estimator 944 is coupled to the diffraction signal processor 946. The first fabrication system 940 is coupled to a metrology processor 1010. The metrology processor 1010 is coupled to the fabrication host processors 1020 and to the metrology data store 1040 if a metrology data store is used. Data 860 from the first fabrication system 940 to the metrology processor 1010 may include the determined profile parameter for transmission to the second fabrication system 970. The metrology data store 1040 may include a library or table of pairs of simulated diffraction signals and corresponding sets of profile parameters, or a trained MLS system that can generate a set of profile parameters from an input measured diffraction signal. Data 860 from the metrology processor 1010 to the first metrology system 940 may include the portion of the data space to be searched in the library by the diffraction signal processor 946 or profile parameters transmitted from the second fabrication system 970.

Referring to FIG. 9, the second fabrication system 970 includes a model optimizer 972, diffraction signal processor 976, a fabrication cluster 978, and a metrology cluster 960. The metrology cluster 980 may include a reflectometer, an ellipsometer, or CDSEM. The real time profile estimator 974 is coupled to the diffraction signal processor 976. Data 862 transmitted to and from the second fabrication system 970 to the metrology processor 1010 are similar to the data 860 transmitted to and from the first fabrication system 940. The first and/or second fabrication systems 940 and 970, may be a photolithography, etch, thermal processing system, metallization, implant, chemical vapor deposition, chemical mechanical polishing, or other fabrication unit.

The diffraction signal processor 946 may comprise one or more servers or multiple central processing units (CPU) within a computer, or multiple-core within a multi-core CPU, or on multiple execution threads on a hyper-threaded CPU/core. Alternatively, the instances of the profile search module may be run in parallel in the diffraction signal processor 946 or distributed in other computers such as the metrology processor 1010, the fabrication host processor 1020, or some remote processor or computer. Similarly, the diffraction signal processor 976 may comprise one or more servers or multiple central processing units (CPU) within a computer, or multiple-core within a multi-core CPU, or on multiple execution threads on a hyper-threaded CPU/core. Instances of the profile search module may be run in the diffraction signal processor 976 or distributed in other computers such as the metrology processor 1010, the fabrication host processor 1020, or some remote processor or computer.

As mentioned above, if metrology data store is used in profile determination, the metrology data store 1040 may be accessible to the diffraction signal processor 946 and 976 directly or remotely by communication lines. Alternatively, the required data store may be loaded to the diffraction signal processor 946 and 976 local storage facilities. Data flows 860 and 862 from the first and second fabrication systems include at least one profile parameter that is used to adjust a process or equipment variable in the previous fabrication system, the current fabrication system, or a later fabrication system.

In particular, it is contemplated that functional implementation of the present invention described herein may be implemented equivalently in hardware, software, firmware, and/or other available functional components or building blocks. For example, the metrology data store may be in computer memory or in an actual computer storage device or medium. Other variations and embodiments are possible in light of above teachings, and it is thus intended that the scope of invention not be limited by this Detailed Description, but rather by Claims following.

We claim:

1. A system for processing requests for wafer structure profile determination from optical metrology measurements off a plurality of structures formed on one or more wafer, the system comprising:
    a diffraction signal processor configured to obtain a plurality of measured diffraction signals of the plurality of structures;
    a diffraction signal distributor coupled to the diffraction signal processor, wherein the diffraction signal processor is configured to transmit the plurality of measured diffraction signals to the diffraction signal distributor; and
    a plurality of profile search servers coupled to the diffraction signal distributor, wherein the diffraction signal distributor is configured to distribute the plurality of measured diffraction signals to the plurality of profile search servers, and wherein the profile search servers are configured to process in parallel the plurality of measured diffraction signals to determine profiles of the plurality of structures corresponding to the plurality of measured diffraction signals.

2. The system of claim 1 further comprising:
    one or more metrology data stores coupled to the diffraction signal processor, wherein the metrology data stores include libraries or tables of simulated diffraction signals and corresponding profiles, and wherein the profile search servers are configured to search for best match simulated diffraction signals to the measured diffraction signals in the one or more metrology data stores.

3. The system of claim 2, wherein the one or more metrology data stores include a data store accessible through a data communications network.

4. The system of claim 1, further comprising:
    one or more trained machine learning systems coupled to the diffraction signal processor, wherein the trained machine learning systems are trained to generate a profile for a measured diffraction signal.

5. The system of claim 1, wherein at least one of the plurality of profile search servers includes:

a data store loading service module configured to load a library or table of pairs of simulated diffraction signals and corresponding sets of profile parameters or configured to use a trained machine learning system, the machine learning system trained to generate a profile from a measured diffraction signal; and a profile search module configured to utilize the data store loading service module to search a best match to the measured diffraction signal in the library or table or configured to use the trained machine learning system to generate a profile from a measured diffraction signal.

6. The system of claim 1, further comprising:

a scheduler coupled to the diffraction signal processor and the diffraction signal distributor, wherein the scheduler is configured to activate one or more instances of a program in one or more available processing threads of one or more of the plurality of profile search servers; and a status checker coupled to the diffraction signal distributor, scheduler, and the plurality of profile search servers, wherein the status checker is configured to check the availability of a profile search server and completion of profile search processing for an assigned diffraction signal.

7. The system of claim 1, wherein at least one of the plurality of profile search servers includes a remotely connected computer.

8. The system of claim 1, wherein at least one of the plurality of profile search servers includes a computer accessible through a private or public network.

9. The system of claim 1 wherein the plurality of profile search servers is implemented with features including statelessness, machine independence, and fault tolerance.

10. The system of claim 1, wherein the plurality of profile search servers is running as a task of a multi-thread or multi-core computer.

11. The system of claim 1, further comprising:

a process fabrication cluster, wherein one or more profile parameters of a profile determined from a measured diffraction signal are used to modify a setting of a device in the process fabrication cluster where the wafer is currently being processed.

12. The system of claim 1, further comprising:

a process fabrication cluster, wherein one or more obtained profile parameters of a profile determined from a measured diffraction signal are transmitted to the process fabrication cluster where the wafer was previously processed.

13. The system of claim 1, further comprising:

a process fabrication cluster, wherein one or more obtained profile parameters of a profile determined from a measured diffraction signal are used to modify at least one process variable in a device in the process fabrication cluster where the wafer was previously processed.

14. The system of claim 1, further comprising:

a process fabrication cluster, wherein one or more profile parameters of a profile determined from a measured diffraction signal are transmitted to the process fabrication cluster where the wafer will be processed later.

15. The system of claim 1, further comprising:

a process fabrication cluster, wherein one or more profile parameters of a profile determined from a measured diffraction signal are used to modify at least one process variable in a device in the process fabrication cluster where the wafer will be processed later.

16. A system for processing a plurality of requests for wafer structure profile determination from optical metrology measurements off a plurality of structures formed on one or more wafers, the system comprising:

a diffraction signal processor configured to obtain a plurality of measured diffraction signals of the plurality of structures;

one or more metrology data stores coupled to the diffraction signal processor, wherein the metrology data stores include libraries or tables of simulated diffraction signals and corresponding profiles;

a diffraction signal distributor coupled to the diffraction signal processor, wherein the diffraction signal processor is configured to transmit the plurality of measured diffraction signals to the diffraction signal distributor; and a plurality of profile search servers coupled to the diffraction signal distributor, wherein the diffraction signal distributor is configured to distribute the plurality of measured diffraction signals to the plurality of profile search servers, and wherein the profile search servers are configured to search for best match simulated diffraction signals to the measured diffraction signals in the one or more metrology data stores.

17. The system of claim 16, further comprising:

one or more schedulers coupled to the diffraction signal distributor, wherein the one or more schedulers are configured to activate a plurality of instances of a program in one or more processing threads of one or more the plurality of profile search servers;

one or more status checkers coupled to the diffraction signal distributors, scheduler, and profile search server, wherein the one or more status checkers are configured to check the availability of a profile search server, completion of profile search processing for an assigned diffraction signal, and presence of a loaded one or more metrology data stores.

18. The system of claim 16, further comprising:

one or more schedulers coupled to the diffraction signal distributor, wherein the one or more schedulers are configured to activate a plurality of instances of a program in one or more processing threads of one or more the plurality of profile search servers;

one or more status checkers coupled to the diffraction signal distributors, scheduler, and profile search server, wherein the one or more status checkers are configured to check the availability of a profile search server and completion of profile search processing for an assigned diffraction signal.

19. The system of claim 18, wherein at least one of the plurality of profile search servers comprises:

a data store loading service module configured to load a library or table of pairs of simulated diffraction signals and corresponding sets of profile parameters or configured to use a trained machine learning system, the machine learning system trained to generate a profile from a measured diffraction signal; and a profile search module configured to utilize the data store loading service module to search for a best match to the measured diffraction signal in the library or table or configured to use the trained machine learning system to generate a profile from a measured diffraction signal.

20. The system of claim 16, wherein at least one of the plurality of profile search servers includes a remotely connected computer.

21. The system of claim 16, wherein at least one of the plurality of profile search servers includes a computer accessible through a private or public network.

22. The system of claim 16, wherein the one or more metrology data stores include a data store accessible through a data communications network.

23. A system for processing a plurality of requests for wafer structure profile determination from optical metrology measurements off a plurality of structures formed on one or more wafers, the system comprising:
- a diffraction signal processor configured to obtain a plurality of measured diffraction signals of the plurality of structures;
- a diffraction signal distributor coupled to the diffraction signal processor, wherein the diffraction signal processor is configured to transmit the plurality of measured diffraction signals to the diffraction signal distributor; and
- a plurality of profile search servers coupled to the diffraction signal distributor, wherein the diffraction signal distributor is configured to distribute the plurality of measured diffraction signals to the plurality of profile search servers, and wherein the profile search servers are configured to process the plurality of measured diffraction signals to determine profiles of the plurality of structures corresponding to the plurality of measured diffraction signals using regression.

24. The system of claim 23, further comprising:
- one or more schedulers coupled to the diffraction signal distributor, wherein the one or more schedulers are configured to activate a plurality of instances of a program in one or more processing threads of one or more the plurality of profile search servers;
- one or more status checkers coupled to the diffraction signal distributors, scheduler, and profile search server, wherein the one or more status checkers are configured to check the availability of a profile search server and completion of profile search processing for an assigned diffraction signal.

25. The system of claim 23, further comprising:
- a process fabrication cluster, wherein one or more profile parameters of a profile determined from a measured diffraction signal are used to modify a setting of a device in the process fabrication cluster where the wafer is currently being processed.

26. The system of claim 23, further comprising:
- a process fabrication cluster, wherein one or more obtained profile parameters of a profile determined from a measured diffraction signal are transmitted to the process fabrication cluster where the wafer was previously processed.

27. The system of claim 23, further comprising:
- a process fabrication cluster, wherein the one or more obtained profile parameters of a profile determined from a measured diffraction signal are used to modify at least one process variable in a device in the process fabrication cluster where the wafer was previously processed.

28. The system of claim 23, further comprising:
- a process fabrication cluster, wherein one or more profile parameters of a profile determined from a measured diffraction signal are transmitted to the process fabrication cluster where the wafer will be processed later.

29. The system of claim 23, further comprising:
- a process fabrication cluster, wherein one or more profile parameters of a profile determined from a measured diffraction signal are used to modify at least one process variable in a device in the process fabrication cluster where the wafer will be processed later.

* * * * *